United States Patent [19]
Roman et al.

[11] Patent Number: 5,967,773
[45] Date of Patent: Oct. 19, 1999

[54] ORTHODONTIC BRACKET WITH SPRING COVER

[75] Inventors: Patrick Roman, Escondido; Richard Bryant, Vista, both of Calif.

[73] Assignee: Orthodontic Design & Production, Vista, Calif.

[21] Appl. No.: 09/218,641

[22] Filed: Dec. 22, 1998

[51] Int. Cl.⁶ ........................................ A61C 3/00
[52] U.S. Cl. .............................. 433/11; 433/13
[58] Field of Search ....................... 433/8, 10, 11, 433/13, 14

[56] References Cited

U.S. PATENT DOCUMENTS

| | | | |
|---|---|---|---|
| 3,854,207 | 12/1974 | Wildman | 433/11 |
| 4,712,999 | 12/1987 | Rosenberg | 433/13 X |
| 5,630,716 | 5/1997 | Hanson | 433/11 X |
| 5,908,293 | 6/1999 | Vandours | 433/11 X |

Primary Examiner—Nicholas D. Lucchesi
Attorney, Agent, or Firm—John J. Murphey

[57] ABSTRACT

A low-profile orthodontic assembly comprising a bracket having a base surface and a top surface, the base surface for mounting to a tooth; at least two pairs of spaced-apart wings, the pairs in mutual faced-apart arrangement, extending upward from the bracket, each wing terminated by a distal end spaced-above the top surface; the distal ends of each the pair of wings joined together by a cross-member to form a passageway thereunder, above the bracket top surface and between the pair of wings; each the pair of wings positioned on opposite sides of a slot formed in the bracket to receive therein an archwire passing along the bracket; and, a cap for assembly with the bracket to cover a portion of the slot including a pair of springy, flexible tongues extending from opposite ends thereof for insertion down into the passageways to spring upward against the cross-members and retain the cap over the archwire with minimal contact therebetween.

21 Claims, 5 Drawing Sheets

ORTHODONTIC BRACKET WITH SPRING COVER

FIELD OF THE INVENTION

This invention pertains to orthodontic appliances employed in the treatment of dental malocclusions. More particularly, it pertains to an orthodonture bracket and cap assembly, used as a part of what is generally known as "braces" mounted on teeth and interconnected by an archwire, to move the teeth into controlled alignment.

BACKGROUND OF THE INVENTION

DESCRIPTION OF THE PRIOR ART

"Every tooth in a man's head is more valuable to him than a diamond". This statement, uttered in Don Quixote I.iii.4, is the basic principal upon which the orthodontic profession is established. Crooked teeth take away beauty, and straightening them brings it back.

The general approach to dental malocclusion correction is to mount a series of brackets on the outside of certain teeth and connect these brackets together with a metal wire, called an "archwire", and other ligating connectors such as wires and rubber bands. The archwire and connectors are then subject to periodic adjustment at the orthodontic practitioner's office to cause the teeth to be pulled, pushed, twisted and otherwise moved into desired alignment over a period of time.

Some problems have arisen in the use of these appliances that have contributed to complaints from patients and failure to achieve desired results. For instance, in order to help retain the archwire in the bracket and not allow it to come loose during eating, speaking and tooth brushing, the archwire is often buried deep in the orthodonture bracket and clamped thereto with a snap-on cap to insure its continued engagement therewith. This often causes increased contact between the archwire and the cap that inhibits movement of teeth on which the bracket is mounted and requires more adjustment of the archwire resulting in more discomfort to the patient. Without continual correction, movement of the teeth to new locations is inhibited and correction of the dental malocclusion is prolonged.

Many brackets employ undercuts in the bracket body on which snap-on caps and rubber "doughnuts" are tethered and become traps for food particles thus promoting tooth decay. While more effort is usually applied to keep these braces clean, through more frequent brushing, the intensified tooth brushing itself often leads to loosening of the archwire cap resulting in slippage of the archwire and loss of the tension necessary to achieve tooth movement.

The snap-on caps usually have curved ends that snap outwardly and downwardly over the ends of cap extensions to hold the archwire in the bracket. The curved ends are then unsnapped using a pick or lever and a fulcrum to pry them upward. Such snapping and prying activity involves much effort, is discomforting to the patient, and can cause injury to adjacent gums and the cheeks and lips should the pick or lever slip during this activity. The constant fidgeting of young children who wear braces also contributes to slips and accidents that may cause painful injury. Further, should the cap or hinge be broken or otherwise damaged during snapping onto the bracket or prying off of the cap ends from the extensions, a new cap must be attached to the bracket, requiring more time and increasing the costs and discomfort to the patient. In addition, the undercuts in the brackets, needed to form the bulbous ends over which the cap ends are snapped, form places where food particles get trapped and are not easily cleaned, even by more frequent brushing.

Finally, any modification of the bracket, to allow more tightening or loosening of the archwire in the bracket, or to relieve the problems associated with prying off the curved ends of the bracket cap, often results in increasing the height of the bracket-cap combination so that the appliance extends further and further from the surface of the tooth. Most orthodonture appliances are placed on the buccal side of the tooth rather than the lingual side, usually because placing them on the lingual side results in injury to the tongue. Raising the height of the appliance on the buccal side results in injury to the cheeks and lips. Therefore, it is desirable to keep the bracket's profile as low as possible.

SUMMARY OF THE INVENTION

This invention is a low-profile orthodontic assembly comprising a bracket having a base surface and a top surface. The base surface is for mounting to a tooth or on a tooth band. At least two pairs of spaced-apart wings are provided, the pairs in mutual faced-apart arrangement and extend upward from the bracket. Each wing is terminated by a distal end spaced-above the top surface of the bracket. The distal ends of each pair of wings are joined together by a cross-member to form a passageway thereunder, above the bracket top surface and between the pair of wings. Each pair of wings are positioned on opposite sides of a slot formed in the bracket to receive therein the archwire passing along the top surface of the bracket. A cap is provided for assembly with the bracket to cover a portion of the slot and includes a pair of springy, flexible tongues extending from opposite ends thereof for insertion down into the passageways to spring upward against the cross-members and retain the cap over the archwire with minimal contact therebetween.

The openings under the cross-member present areas for fluid flow for the patient to swish water and mouthwash through to remove particles of food before they begin to putrify. In addition, the cap rests upon spaced-apart chamfers formed on the inside edges of the wings so that the cap is always centered and the buccal height of the bracket or profile is maintained at a minimum and does not interfere with tooth brushing, eating, etc. Further, the tongues extending downward from the cap allow the cap to be squeezed with a special tool resembling pinchers during application and removal so that the cap is merely set down on the buccal side of the bracket and the tongues allowed to pass down into the openings under the cross-members and later hold the cap onto the bracket by spring force. Removal is easily accomplished in a reversal of the same way. This eliminates the action of snapping on and prying off the cap with lever and fulcrum and reduces shock to the teeth, discomfort to the patient, and potential danger to surrounding tissue.

The cap may also contain a downwardly-directed fold that bears down on the archwire to increase the contact with it for certain application where restricted movement of the archwire is desired. The method of installing the cap is novel in that the tongues extending from the cap require pinching to bend them prior to installing the cap so that the tongues are inserted into the spaced-apart openings under the cross-members. This is in contrast to the present use of caps that snap over top of the wings requiring levers and fulcrums to pry the cap off the bracket.

Accordingly, the main object of this invention is an orthodontic appliance employed in the treatment of dental malocclusions that is of low profile and contains a cap that is held onto the base by spring action other than outwardly and downwardly, snap-over action. Other objects of the invention include an orthodontic appliance that has a removable cap that can be easily modified to increase or decrease contact with the archwire; an appliance that allows the cap to be sprung into and out of contact with the bracket without snapping action or prying action; an appliance that is low in profile due to the unique design of the crossmembers on the bracket and is retained centered in the bracket because of the side wall design; an appliance that contains areas for flow for fluids, such as water and mouth wash, to pass through the assembly to wash away particles of food that would otherwise decay and cause bad breath as well as attack the tooth on which the bracket is mounted.

These and other objects of the invention will become more clear when one reads the following specification, taken together with the drawings that are attached hereto. The scope of protection sought by the inventors may be gleaned from a fair reading of the claims that conclude this specification.

DESCRIPTION OF THE PREFERRED EMBODIMENT

Figure 1:
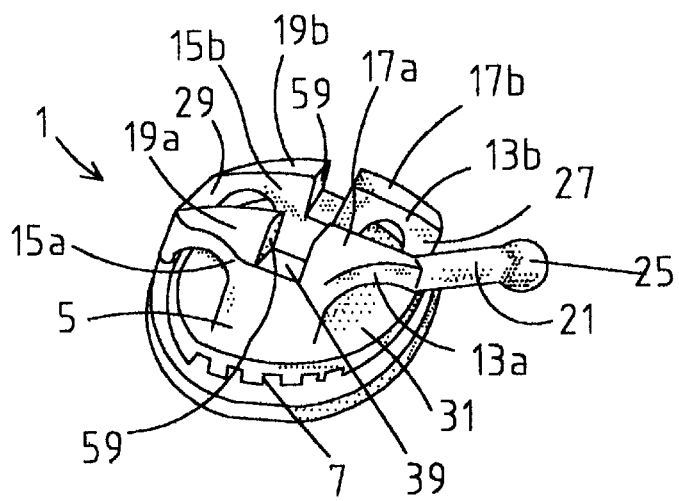
FIG. 1 is a perspective view of the preferred embodiment of this invention.
Figure 2:
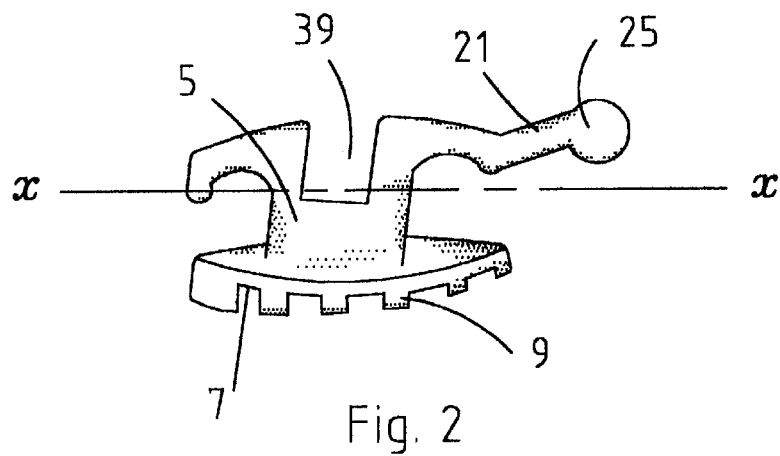
FIG. 2 is an end view of the embodiment shown in FIG. 1.
Figure 3:
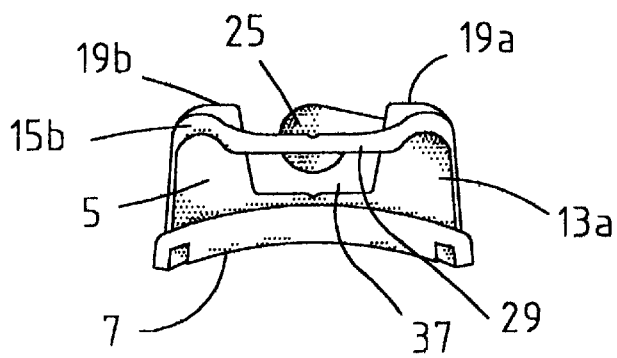
FIG. 3 is a left side view of the embodiment shown in FIG. 1.
Figure 4:
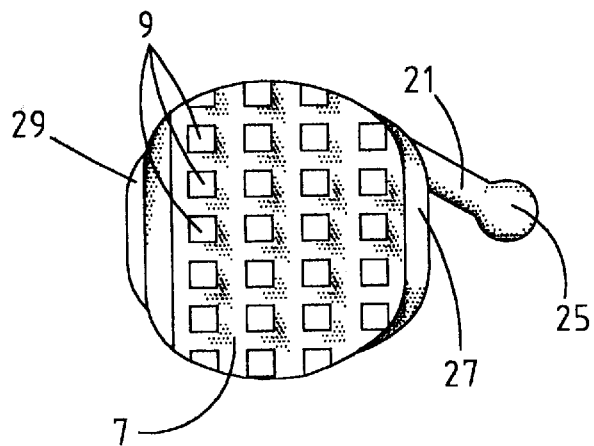
FIG. 4 is a bottom view of the embodiment shown in FIG. 1.

Turning now to the drawings wherein elements are identified by numbers and like elements are identified by like numbers throughout the 15 drawings, FIGS. 1, 2 and 3 show the preferred embodiment of this invention noted as 1. Invention 1 comprises a bracket 5, which includes a base surface 7, preferably slightly curved for tight abutment against the tooth surface and which may include a plurality of small projections or irregularities 9 for combining with a bonding agent (not shown) to provide a strong joint with the tooth. Bracket 5 is preferably made of stainless steel, titanium, or plastic and is shown to have a somewhat overall rectangular shape, however, other shapes, such as circular, elliptical, rhomboidal, trapezoidal and irregular shapes are also contemplated herein.

At least two pairs of wings, 13a, 13b and 15a, 15b, the wings in each pair in spaced-apart arrangement, extend upward or outward (depending upon the orientation of bracket 5) in mutual, paired, faced-apart arrangement from bracket 5. Each wing is terminated by a distal end, namely 17a and 17b (for wings 13a, 13b) and 19a and 19b (for wings 15a, 15b) each said distal end spaced apart from another wing and distal end and spaced-above said bracket upper surface. Said distal ends terminate said wings apart from each other and spaced-above bracket 5 as shown in FIGS. 1, 2 and 3. When bracket 5 has a rectangular shape, it is preferred that wing pairs 13a, 13b and 15a, 1 5b extend from the corners thereof. On brackets used on cuspids or bicuspids, an arm or elastic hook 21, terminated by a spherical knob 25, extends outward from the distal end of wing 13a, as shown in FIGS. 1, 2, 4 and 5, for the purpose of anchoring a rubber band (not shown) or other tooth adjustment device as is already known in the prior art.

Figure 5:
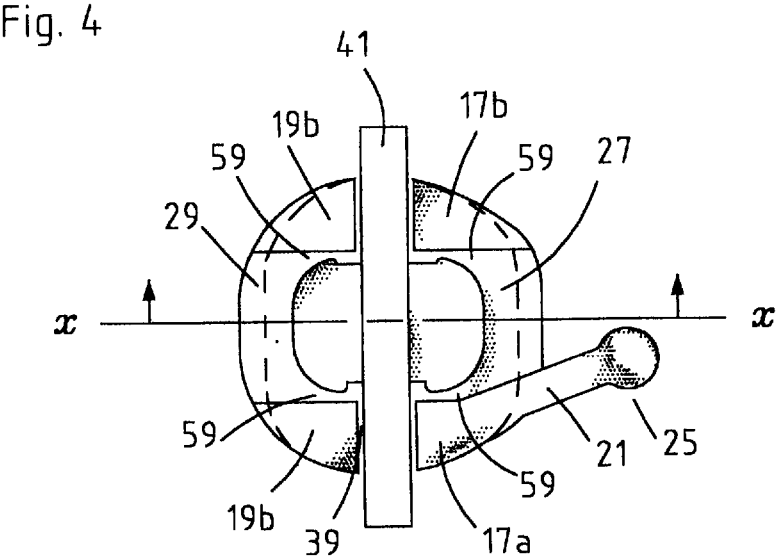
FIG. 5 is top view of the embodiment shown in FIG. 1 with an archwire shown located therein.

A cross-member 27 spans distal ends 17a and 17b of wing pair 13a, 13b while a similar cross-member 29 spans distal ends 19a and 19b of wing pair 15a, 15b as shown in FIGS. 1, 3, 5 and 6. Cross-members 27 and 29 are preferably made of the same material making up wings 13a, 13b, 15a and 15b. Their presence provides strength to said wings and reduces archwire slot deformation as will be shown later. As shown in FIGS. 1, 2 and 3, the smooth upper or top surface 31 of bracket 5, wings 13a, 13b and 15a, 15b, and cross-members 27 and 29 form passageways 33 and 37, respectively, on both sides of bracket 5 and on the top surface thereof that allow flow of fluid (mouthwash, saliva, water, etc.) completely across bracket upper surface 31, or from interior said bracket to exterior thereof. As shown in FIGS. 5 and 7, both passageways 33 and 37 lie in spaced-apart arrangement on opposite sides of a slot 39 formed in bracket 5 that passes across upper bracket surface 31, preferably orthogonal to an axis x—x (FIGS. 2 and 5) passing through the centers of passageways 33 and 37.

An archwire 41 is provided for placement in slot 39, as shown in FIGS. 5 and 7, whose function has been previously described. Archwire 41 can be rectangular, circular, or of some other configuration in cross-section and this invention will work favorably with all such geometries. Slot 39 may be deeper than the vertical height of archwire 41, as shown in FIG. 7 or it may be shallower that the vertical height of archwire 37 and both embodiments are fully contemplated in this invention.

Figure 8:
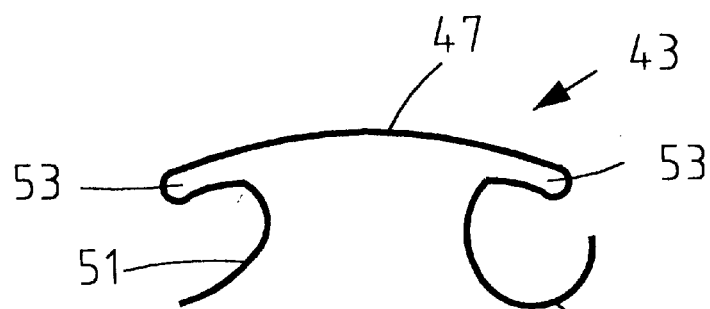
FIG. 8 is a side view of one embodiment of a cap useful in this invention.
Figure 9:
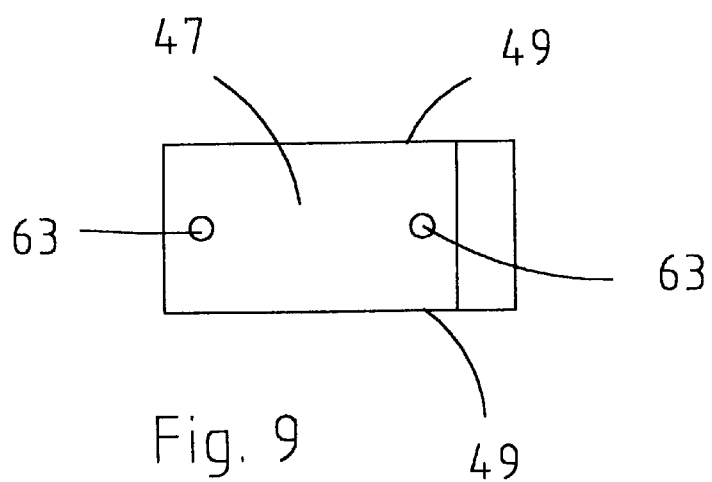
FIG. 9 is a top view of the embodiment shown in FIG. 8.
Figure 10:
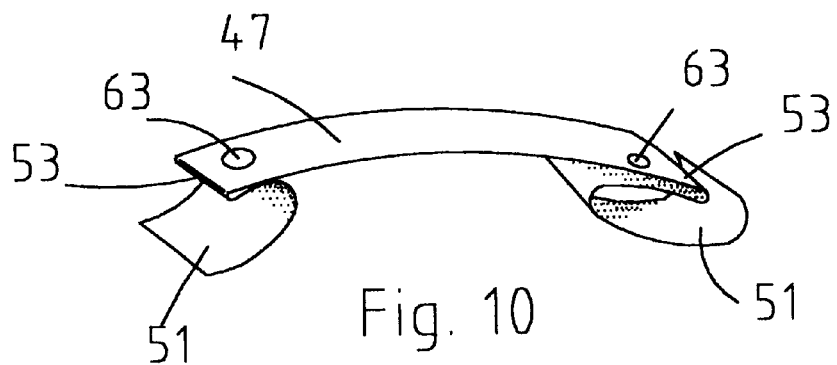
FIG. 10 is a perspective view of the embodiment shown in FIGS. 8 and 9.
Figure 11:
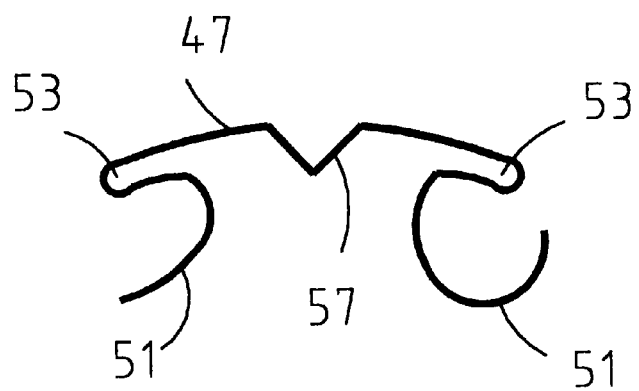
FIG. 11 is a side view of a modification of the embodiment shown in FIG. 8.
Figure 12:
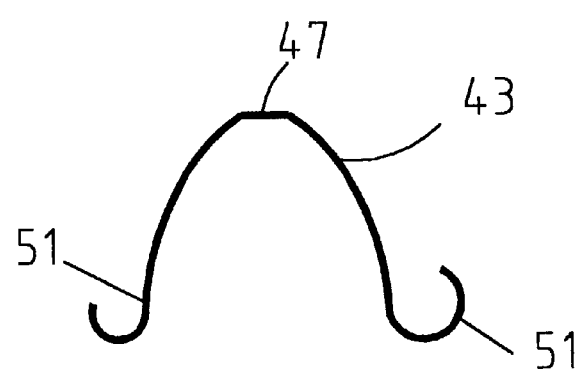
FIG. 12 is a side view of another embodiment of a cap useful in this invention.
Figure 13:
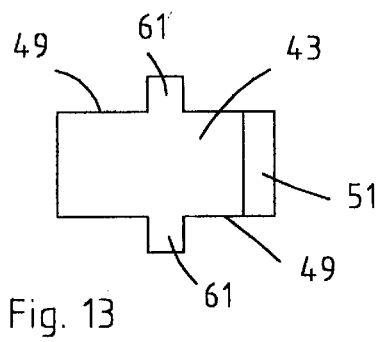
FIG. 13 is a top view of the embodiment shown in FIG. 12.
Figure 14:
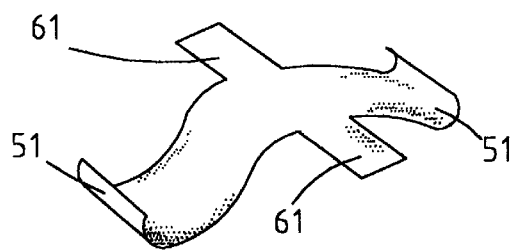
FIG. 14 is a perspective view of the embodiments shown in FIG. 12 and 13.

A cap 43 is provided for covering over at least part of slot 39 as well as at least a portion of archwire 41 that is inserted therein. One embodiment of cap 43 is shown in FIGS. 8,9 and 10 with a modified embodiment thereof shown in FIG. 11 while a different embodiment is shown in FIGS. 12, 13 and 14. Cap 43 is preferably made of a thin, springy foil of stainless steel or other such material, and is defined by a central portion 47, bounded by opposed side edges 49 and having a pair of springy, flexible tongues 51, extending from tightly reversed folds 53 located at opposite ends of central portion 47, that extend preferably downward and outward therefrom.

In assembling cap 43 with bracket 5, cap tongues 51 are pinched or squeezed downward and/or toward each other, and cap 43 lowered onto bracket 5 over slot 39 and in between wing pairs 13a, 13b and 15a, 15b so that tongues 51 slide downward under crossmembers 27 and 29 and outward into passageways 33 and 37 and then spring upward into contact with cross-members 27 and 29 to be held therein under the tension or bias nature of cap 43 as shown in FIG. 7.

Figure 15:
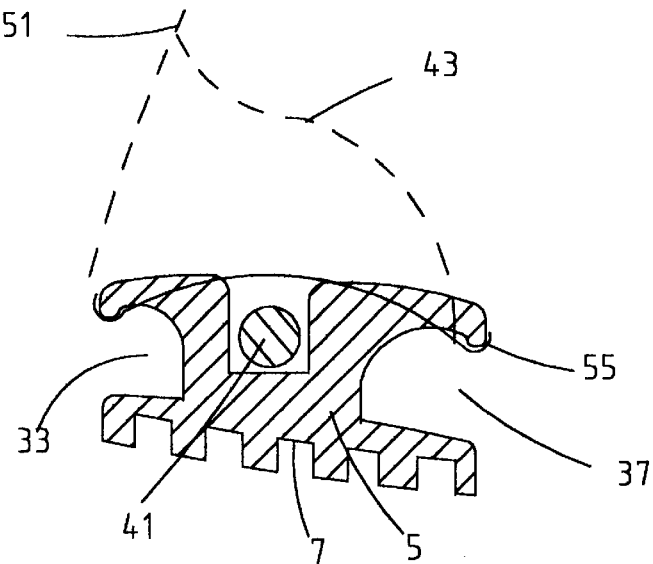
FIG. 15 is a sectional side view of another embodiment of the invention showing the archwire to have a circular cross-section.

While both tongues 51 may be formed of a length and curvature to be inserted and fully removed from bracket 5 following initial installation, one of tongues 51 may be made longer and/or bent further or otherwise formed to encircle one of cross-members 27 or 29 to act, after initial installation, as a hinge or long term pivotal connector 55 between cap 43 and bracket 5, as shown in FIG. 15. In this configuration, shown in FIG. 15, cap 43 need only be unhooked at one end and rotated upward, as shown by the dotted lines, to an "opened" configuration, thus making adjustment to the entire assembly faster and with less invasion to the patient's mouth.

In another embodiment of this invention, shown in FIGS. 7 (dotted outline) and 11, a partial downwardly-directed fold 57 is formed in cap 43, preferably in cap central portion 47, and aligned to depend into and follow slot 39, where archwire 41 is received, to provide an area of increased contact therebetween.

Figure 6:
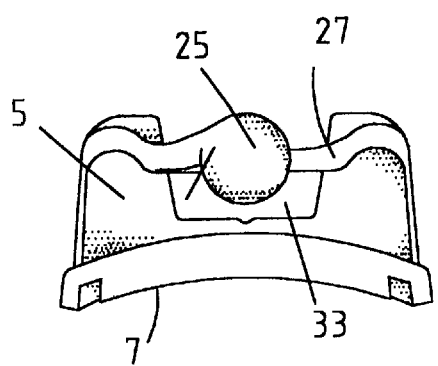
FIG. 6 is a right side view of the embodiment shown in FIG. 1.
Figure 7:
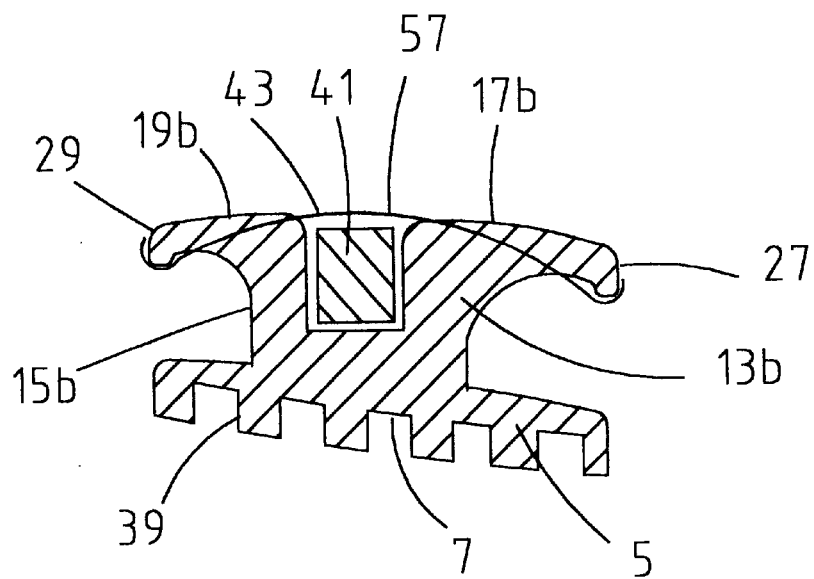
FIG. 7 is a sectional-side view taken along lines 7—7 in FIG. 5 and showing the arch wire to have a rectangular cross-section.

To maintain a low-profile or silhouette, as desired in this art, the inside wall surfaces 13a, 13b, 15a, and 15b contain chamfered surfaces 59 that are slightly beveled inward from top to bottom, as shown in FIGS. 3, 5 and 6. This chamfer or beveling causes cap side edges 49 to contact said surfaces 59 and center said cap at a position thereagainst to centralize said cap between said wings. This centering aspect of the invention will cause cap 43 to continue to remain centered on said bracket 5 throughout use of the bracket assembly.

Preferably, tongues 51 are made slightly narrower than the width of passageways 33 and 37 as well as thinner than the height of passageways 33 and 37 so that, following insertion of tongues 51 into passageways 33 and 37, there remains additional room through passageways 33 and 37, as shown in FIG. 15, to allow water, mouthwash and other cleaning agents to flow therethrough to flush out particles of food and other material that may have become trapped in bracket 5. This allows the assembly to be more easily cleaned that those of the prior art.

In a separate embodiment shown in FIGS. 12, 13 and 14, this invention further includes a pair of tabs 61 extending outward from opposite sides of cap 39, and specifically cap central portion 47, forming an angle such as orthogonal to tongues 51, for covering that portion of slot 39 remaining outside cap central portion 47. Tabs 61 preferably are not spring-loaded nor capable of entrance into slot 39 or into passageways 33 and 37 and thus do not aid in retaining cap 43 on bracket 5 but merely cover that portion of archwire 41 that is not covered by cap central portion 47.

The novel method of this invention of anchoring archwire 41 on a tooth comprises the first step of attaching bracket 5 to a tooth or tooth band. The next step is to thread archwire 41 into slot 39 between said pairs 13a, 13b and 15a, 15b of wings and across bracket 5. The next step is to provide cap 43, having tongues 51 extending from opposite sides thereof, and then pinch tongues 51 downward and/or together and lower cap 43 onto bracket 5 and allow tongues 51 to enter passageways 33 and 37 and thereafter release them to allow the spring action of cap 43 and tongues 51 to hold cap 43 over archwire 41 with minimal contact therebetween. To enable tongues 51 to be pinched as required, a pair of apertures 63 are formed in cap 43, as shown in FIGS. 9 and 10, to receive therein the pinching portions (not shown) of the tool used to pinch cap 43. The number, shape, size and location of said apertures 63 may be changed to fit the exigencies of the situation and such changes are fully contemplated in this invention.

In another embodiment of this novel method, the step of pinching pair 51 of flexible tongues downward, to allow them to enter passageways 33 and 37, under cross-members 27 and 29, and thereafter releasing them to allow the spring action of cap 43 and tongues 51 to retain cap 43 on bracket 5 and over archwire 41, with minimal contact therebetween, is followed by the step of bending one of tongues 51 upward about cross-member 27 or 29 to form a pivotal connection therebetween. In this embodiment, cap 43 becomes pivoted about one cross-member.

In a still further embodiment of this novel method, the step of providing springy cap 43 with flexible tongues 51 is followed by the step of placing a downwardly-directed fold 57 in cap 43, along the portion thereof that will reside above archwire 41, so that cap 43 will provide additional contact with archwire 41 when said cap is inserted in place thereover.

While the invention has been described with reference to a particular embodiment, those skilled in the art will be able to make various modifications to the described invention without departing from the true spirit and scope thereof. It is intended that all combinations of elements and steps which perform substantially the same function in substantially the same way to achieve substantially the same result are within the scope of this invention.

What is claimed is:

1. A low-profile orthodontic assembly comprising:
   a) a bracket having a base surface and a top surface, said base surface for mounting to a tooth or a tooth band;
   b) at least two pairs of spaced-apart wings, said pairs in mutual faced-apart arrangement, extending upward from said bracket, each wing terminated by a distal end spaced-above said top surface;
   c) said distal ends of each said pair of wings joined together by a crossmember to form a passageway thereunder, above said bracket top surface and between said pair of wings;
   d) each said pair of wings positioned on opposite sides of a slot formed in said bracket to receive therein an archwire passing along said bracket; and,
   f) a cap for assembly with said bracket to cover a portion of said slot including a pair of springy, flexible tongues extending from opposite ends thereof for insertion down into said passageways to spring upward against said cross-members and retain said cap over said archwire with minimal contact therebetween.

2. The orthodontic assembly of claim 1 wherein said base is rectangular in outline.

3. The orthodontic assembly of claim 1 wherein said base has a curved outline.

4. The orthodontic assembly of claim 1 wherein said base has a rhomboidal outline.

5. The orthodontic assembly of claim 1 wherein said base has a trapezoidal outline.

6. The orthodontic assembly of claim 5 wherein said passageways are larger in cross-sectional area than the cross-sectional area of said cap tongues so that, following insertion of said cap tongues into said passageways, there remains additional room for flow of liquid through said passageways.

7. The orthodontic assembly of claim 1 wherein said base has an irregular outline.

8. The orthodontic assembly of claim 1 wherein said bracket is rectangular in outline and said pairs of wings extend outward from the corners of said bracket.

9. The orthodontic assembly of claim 8 wherein said cap has a partial downwardly-directed fold formed therein and arranged to depend toward and contact the archwire in said slot to provide an area of increased contact between said cap and the archwire to increase the contact therebetween.

10. The orthodontic assembly of claim 1 wherein said passageways created under said cross-members and between said wings pass completely across said top surface of said bracket from interior said bracket to exterior thereof to allow water and liquids to flow completely therethrough.

11. The orthodontic assembly of claim 1 wherein said slot formed in said bracket, to receive therein an archwire passing therealong, is deeper than the vertical height of the archwire received therein so that the top surface of the archwire lies outside of contact with said cap.

12. The orthodontic assembly of claim 1 further including chamfer surfaces formed on interior sides of said pairs of wings and arranged to receive said cap at a position thereagainst to centralize said cap between said wings.

13. The orthodontic assembly of claim 1 further including a pair of tabs extending from opposite sides of said cap, for covering that portion of the archwire that passes between said pairs of bridged extensions, outside of said cap and across said upper surface of said bracket.

14. The orthodontic assembly of claim 13 wherein said pair of tabs are arranged orthogonal to said tongues.

15. The orthodontic assembly of claim 1 further including at least one aperture, formed in said cap, for cooperative connection with a device to effect a pinching movement in said cap for aid in inserting said cap in place in said bracket.

16. A low-profile orthodontic assembly comprising:
   a) a bracket having a slightly curved base surface and a smooth upper surface, said base surface containing a plurality of irregularities for combining with a bonding agent to provide a strong joint with a tooth or a tooth band;
   b) at least two pairs of spaced-apart wings, said pairs in mutual faced-apart arrangement, extending outward from said bracket, each wing terminated by a distal end spaced apart from another wing and spaced-above said bracket upper surface;
   c) said distal ends of each said pair of wings joined together by a crossmember to form a passageway thereunder, above said bracket upper surface and between said pair of wings;
   d) each said pair of wings positioned on opposite sides of a slot formed in said bracket upper surface to receive therein an archwire passing along said bracket; and,
   e) a cap for assembly with said bracket to cover a portion of said slot including a pair of springy, flexible tongues extending from tightly reversed folds, located at opposite ends of said cap, for insertion down into said passageways to spring upward against said cross-members and retain said cap over said archwire with minimal contact therebetween.

17. The low-profile orthodontic assembly of claim 16 wherein said passageways are larger in cross-sectional area than the cross-sectional area of said cap tongues so that, following insertion of said cap tongues into said passageways, there remains additional room for flow of liquid therethrough.

18. A method of anchoring an archwire on a tooth comprising the steps of:
   a) attaching a bracket by its base surface to the surface of a tooth, said bracket having two pairs of wings in faced-apart arrangement extending outward therefrom, each wing terminated by a distal end spaced-apart from said bracket, said distal ends of each said pair of wings joined together by a cross-member to form a passageway thereunder, above a top surface formed on said bracket and between said pair of wings, each said pair of wings positioned on opposite sides of a slot formed in said bracket to receive therein an archwire passing along said bracket;
   b) threading an archwire into said slot between said pairs of wings and across said bracket;
   c) providing a cap having a pair of flexible tongues extending from opposite ends thereof; and,
   d) pinching said pair of flexible tongues downward to allow them to pass into said passageways under said cross-members to center said cap over said bracket; and,
   e) releasing said tongues to allow the spring action thereof to hold said cap on said bracket and over said archwire with minimal contact therebetween.

19. The method of anchoring an archwire of claim 18 wherein the step of pinching said pair of flexible tongues downward to allow them to pass into said passageways under said cross-members and thereafter releasing them to allow the spring action of said tongues to hold said cap down against said bracket and over the archwire with minimal contact therebetween is followed by the step of bending one of said tongues to encircle one of said cross-members to act as a hinge or long term pivotal connector between said cap and said bracket.

20. The method of anchoring an archwire on a tooth of claim 18 wherein said step of providing said cap having a pair of flexible tongues extending from opposite ends thereof is preceded by the step of placing a downwardly-directed fold in said cap, along the portion thereof that will reside above the archwire, so that said cap will provide additional contact between the archwire and said cap when said cap is inserted in place thereover.

21. The method of anchoring an archwire of claim 18 wherein the step of providing a cap having a pair of flexible tongues extending from opposite end thereof includes the additional step of forming a pair of tabs on said cap, said tabs extending from opposite sides of said cap for covering over more of the archwire when said cap is assembled with said bracket.

* * * * *